(12) United States Patent
Nagayasu et al.

(10) Patent No.: US 9,663,422 B2
(45) Date of Patent: May 30, 2017

(54) METHOD FOR PRODUCING LUBRICATING-OIL BASE OIL

(71) Applicant: JX NIPPON OIL & ENERGY CORPORATION, Tokyo (JP)

(72) Inventors: Yoshiyuki Nagayasu, Tokyo (JP); Marie Iwama, Tokyo (JP); Kazuaki Hayasaka, Tokyo (JP); Koshi Takahama, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 312 days.

(21) Appl. No.: 14/388,377

(22) PCT Filed: Mar. 29, 2013

(86) PCT No.: PCT/JP2013/059651
§ 371 (c)(1),
(2) Date: Sep. 26, 2014

(87) PCT Pub. No.: WO2013/147210
PCT Pub. Date: Oct. 3, 2013

(65) Prior Publication Data
US 2015/0051429 A1 Feb. 19, 2015

(30) Foreign Application Priority Data
Mar. 30, 2012 (JP) .................................. 2012-082305

(51) Int. Cl.
| | | |
|---|---|---|
| *C07C 5/27* | (2006.01) | |
| *C07C 4/06* | (2006.01) | |
| *C10G 45/64* | (2006.01) | |
| *B01J 29/068* | (2006.01) | |
| *C10G 45/58* | (2006.01) | |
| *C10G 65/04* | (2006.01) | |
| *C07C 5/02* | (2006.01) | |

(52) U.S. Cl.
CPC ........... *C07C 5/2775* (2013.01); *B01J 29/068* (2013.01); *C07C 4/06* (2013.01); *C07C 5/02* (2013.01); *C10G 45/58* (2013.01); *C10G 45/64* (2013.01); *C10G 65/043* (2013.01); *B01J 2229/42* (2013.01); *C07C 2529/068* (2013.01); *C10G 2300/301* (2013.01)

(58) Field of Classification Search
None
See application file for complete search history.

(56) References Cited

U.S. PATENT DOCUMENTS

| | | |
|---|---|---|
| 7,132,042 B2 | 11/2006 | Genetti et al. |
| 7,282,137 B2 | 10/2007 | Cody et al. |
| 2004/0065588 A1 | 4/2004 | Genetti et al. |
| 2004/0108249 A1 | 6/2004 | Cody et al. |
| 2010/0016195 A1* | 1/2010 | Shirahama ........... C10M 101/02 508/382 |
| 2011/0042267 A1 | 2/2011 | Hayasaka |
| 2011/0270010 A1 | 11/2011 | Hayasaka et al. |
| 2011/0319685 A1 | 12/2011 | Krishna et al. |

FOREIGN PATENT DOCUMENTS

| | | | |
|---|---|---|---|
| CN | 1703273 | 11/2005 | |
| CN | 1703488 | 11/2005 | |
| CN | 101939102 | 1/2011 | |
| EP | 0225053 A1 * | 6/1987 | ........... C10G 65/043 |
| JP | 2006-502297 | 1/2006 | |
| JP | 2008-133369 | 6/2008 | |
| JP | 2010-155187 | 7/2010 | |
| WO | 2012/005976 | 1/2012 | |

OTHER PUBLICATIONS

English Translation of the International Preliminary Report of Patentability for Application No. PCT/2013/059651, which was mailed Oct. 9, 2014.
Chinese Office Action for 201380017210.5, mailed May 6, 2015.
Japanese Notice of Allowance for Application No. 2012-082305, mailed May 26, 2015.
International Search Report of PCT/JP2013/059651 mailed May 7, 2013.

* cited by examiner

*Primary Examiner* — Sharon Pregler
*Assistant Examiner* — Alyssa L Cepluch
(74) *Attorney, Agent, or Firm* — Greenblum and Bernstein, P.L.C.

(57) ABSTRACT

A method for producing a lubricant base oil which comprises a first step of carrying out isomerization dewaxing by contacting, in the presence of hydrogen, a hydrocarbon oil containing normal paraffin having a boiling point of 360° C. or higher, with a hydroisomerization catalyst under conditions such that a cracking rate defined in the following formula (1) is 10 mass % or less, and a second step of carrying out the above isomerization dewaxing by temporarily switching the above conditions to conditions such that the cracking rate is 13 mass % or more.

$$\text{Cracking rate (mass \%)} = [(C_1 - C_2)/C_1] \times 100 \qquad (1)$$

wherein $C_1$ represents the mass ratio of a fraction having a boiling point of 360° C. or higher in the above hydrocarbon oil, and $C_2$ represents the mass ratio of the fraction having a boiling point of 360° C. or higher in the above hydrocarbon oil after the isomerization dewaxing.

4 Claims, No Drawings

US 9,663,422 B2

METHOD FOR PRODUCING LUBRICATING-OIL BASE OIL

TECHNICAL FIELD

The present invention relates to a method for producing a lubricant base oil.

BACKGROUND ART

Among petroleum products, for example, lubricant oils, gas oils, jet fuels, and the like are products in which cold flow property is regarded as important. For this reason, it is desirable that base oils used for these products be such that waxy components such as normal paraffins or slightly branched isoparaffins, which are responsible for deteriorating the cold flow property, have been completely or partially removed, or converted to components other than waxy components.

An example of a known dewaxing technique for removing waxy components from hydrocarbon oils is a method wherein waxy components are extracted using a solvent such as liquefied propane or MEK. However, this method has problems in that the operating costs are high, and the product yield is reduced by the removal of waxy components.

A method for converting waxy components in a hydrocarbon oil to non-waxy components using a catalyst from the above solvent dewaxing process, a so-called isomerization dewaxing technique, is widely known as a method for improving the yield of a lubricant base oil.

On the other hand, an example of a known dewaxing technique for converting waxy components in a hydrocarbon oil to non-waxy components is isomerization dewaxing in which the hydrocarbon oil is contacted, in the presence of hydrogen, with a hydroisomerization catalysts having bifunction capable of hydrogenation-dehydrogenation and isomerization, thereby isomerizing normal paraffins in the hydrocarbon oil to isoparaffins (e.g., Patent Document 1).

CITATION LIST

Patent Literature

Patent Document 1: Japanese Unexamined Patent Application Publication No. 2006-502297

SUMMARY OF INVENTION

Technical Problem

While the isomerization dewaxing is a very effective method for improving the cold flow property of hydrocarbon oils, the hydrocarbon oil cracking (conversion to a lighter product) also proceeds at the time of isomerization dewaxing of hydrocarbon oils since the hydroisomerization catalysts used for the isomerization dewaxing are capable of both isomerization and hydrocarbon cracking. To obtain a desired fraction in good yield, the conditions for isomerization dewaxing are usually selected such that the cracking of hydrocarbon oils proceeds as little as possible.

The isomerization dewaxing is typically carried out continuously by passing hydrocarbon oils and hydrogen through an isomerization dewaxing reactor equipped with a hydroisomerization catalyst. Thus, it is desired that hydroisomerization catalysts have longer life performance since hydroisomerization catalysts with short catalyst life require costs and trouble for catalytic exchange.

Under the circumstances, the present invention has an object to provide a method for producing a lubricant base oil capable of achieving the longer life performance of hydroisomerization catalysts and providing a lubricant base oil stably for an extended period of time.

Solution to Problem

A method for producing a lubricant base oil according to the present invention comprises a first step of carrying out isomerization dewaxing by contacting, in the presence of hydrogen, a hydrocarbon oil containing normal paraffin having a boiling point of 360° C. or higher, with a hydroisomerization catalyst under conditions such that the cracking rate defined in the following formula (1) is 10 mass % or less, and a second step of carrying out the above isomerization dewaxing by temporarily switching the above conditions to conditions such that the cracking rate is 13 mass % or more.

$$\text{Cracking rate (mass \%)} = [(C_1 - C_2)/C_1] \times 100 \quad (1)$$

wherein $C_1$ represents the mass ratio of a fraction having a boiling point of 360° C. or higher in the above hydrocarbon oil, and $C_2$ represents the mass ratio of the fraction having a boiling point of 360° C. or higher in the above hydrocarbon oil after the isomerization dewaxing.

According to the present invention, the first step and the second step when combined together enable hydroisomerization catalysts to have longer life performance and stably provide a lubricant base oil for an extended period of time.

According to the findings by the present inventors, when isomerically dewaxing a hydrocarbon oil containing normal paraffin having a boiling point of 360° C. or higher, a cause of the low activation of a hydroisomerization catalyst is the drift of the hydrocarbon oil, and thus in the present invention, while the isomerization dewaxing is carried out with the sufficiently suppressed hydrocarbon oil cracking in the first step, the drift caused in the first step is eliminated by the temporarily performed second step, thereby achieving the longer catalyst life performance.

More specifically, according to the present invention, when the isomerization dewaxing is carried out under conditions such that intentionally a cracking rate is 13 mass % or more in the second step, it is conceived that a low viscous hydrocarbon oil having high flow property is produced in the isomerization dewaxing reactor and the circulation of this low viscous hydrocarbon oil in the isomerization dewaxing reactor eliminates the above drift.

In an embodiment of the present invention, the above hydroisomerization catalyst is a catalyst which contains a zeolite having a one-dimensional porous structure including a 10-membered ring, a support containing a binder, and platinum and/or palladium supported on the support, wherein the zeolite is derived from an ion-exchanged zeolite obtained by ion-exchanging an organic template-containing zeolite containing an organic template and having a one-dimensional porous structure including a 10-membered ring in a solution containing ammonium ions and/or protons. In the embodiment, the carbon content of the hydroisomerization catalyst may be 0.4 to 3.5% by mass. In the embodiment, the micropore volume per unit mass of the above catalyst may be 0.02 to 0.12 cc/g, and the micropore volume per unit mass of the zeolite contained in the above catalyst may be 0.01 to 0.12 cc/g.

Such a hydroisomerization catalyst is not likely to suffer from the catalyst deactivation caused by changes in the isomerization dewaxing conditions, more remarkably achieving the longer catalyst life performance which is the effect of the present invention.

In the method for producing a lubricant base oil according to the present invention, for example, while performing the first step continuously, the second step can be temporarily carried out at the predetermined intervals.

Advantageous Effects of Invention

According to the present invention, a method for producing a lubricant base oil capable of achieving the longer life performance of hydroisomerization catalysts and providing a lubricant base oil stably for an extended period of time is provided.

DESCRIPTION OF EMBODIMENTS

Hereinafter, preferred embodiments of the present invention are described.

The method for producing a lubricant base oil of the present embodiment comprises the first step of carrying out the isomerization dewaxing by contacting, in the presence of hydrogen, a hydrocarbon oil containing normal paraffin having a boiling point of 360° C. or higher, with a hydroisomerization catalyst under conditions such that the cracking rate defined in the following formula (1) is 10 mass % or less, and the second step of carrying out the above isomerization dewaxing by temporarily switching the above conditions to conditions such that the cracking rate is 13 mass % or more.

$$\text{Cracking rate (mass \%)} = [(C_1 - C_2)/C_1] \times 100 \quad (1)$$

wherein $C_1$ represents the mass ratio of a fraction having a boiling point of 360° C. or higher in a hydrocarbon oil, and $C_2$ represents the mass ratio of the fraction having a boiling point of 360° C. or higher in a hydrocarbon oil after the isomerization dewaxing.

$C_1$ and $C_2$ can be calculated from the results obtained by analyzing a feedstock hydrocarbon oil and the hydrocarbon oil after the isomerization dewaxing respectively using gas chromatography.

(First Step)

In the first step (hereinafter in some cases referred to as "isomerization treatment step"), the isomerization dewaxing is carried out by contacting, in the presence of hydrogen, a hydrocarbon oil containing normal paraffin having a boiling point of 360° C. or higher, with a hydroisomerization catalyst. In the first step, the isomerization dewaxing is carried out under conditions such that the cracking rate defined in the formula (1) is 10 mass % or less. The cracking rate in the first step is preferably 8 mass % or less, more preferably 5 mass % or less.

The catalysts commonly used for the hydrogenation isomerization, more specifically, catalysts in which a metal having a hydrogenation activity is supported on an inorganic support, can be used as the hydroisomerization catalyst.

The metal having the hydrogenation activity used for the hydroisomerization catalyst is one or more metals selected from the group consisting of the metals belonging to Group 6, Group 8, Group 9 and Group 10 of the periodic table. Specific examples of these metals include noble metals such as platinum, palladium, rhodium, ruthenium, iridium, osmium, and the like, or cobalt, nickel, molybdenum, tungsten, iron, and the like, with platinum, palladium, nickel, cobalt, molybdenum and tungsten being preferable, and platinum and palladium being further preferable. A plurality of these metals are preferably used in combination, and, in that case, examples of the preferred combination include platinum-palladium, cobalt-molybdenum, nickel-molybdenum, nickel-cobalt-molybdenum, nickel-tungsten, and the like.

Examples of the inorganic support composing the hydroisomerization catalyst include metal oxides such as alumina, silica, titania, zirconia, boria, or the like. These metal oxides may be used singly or in a mixture of two or more, or as a complex metal oxide such as silica alumina, silica zirconia, alumina zirconia, an alumina boria, or the like. These above inorganic supports are preferably, in the light of effectively promoting the hydrogenation isomerization of normal paraffin, complex metal oxide having solid acids such as silica alumina, silica zirconia, alumina zirconia, alumina boria, or the like. The inorganic support may contain a small amount of zeolite. The inorganic support may further contain a binder for the purpose of improving the moldability and mechanical strengths of the support. Preferable examples of the binder include alumina, silica, magnesia, and the like.

The content of metal having the hydrogenation activity in the hydroisomerization catalyst is, when the metal is the above noble metal, preferably about 0.1 to 3 mass % on a mass basis of the support as the metal atom. When the metal is a metal other than the above noble metals, it is preferred that the content be about 2 to 50 mass % on a mass basis of the support as the metal oxide. When a content of the metal having the hydrogenation activity is below the above lower limit value, the hydrogenation isomerization tends not to sufficiently proceed. Conversely, when a content of the metal having the hydrogenation activity exceeds the above upper limit value, the dispersion of metal having the hydrogenation activity reduces, causing a tendency to reduce the catalytic activity thereby raising the catalyst cost.

The hydroisomerization catalyst may be a catalyst which supports at least one metal selected from the elements belonging to Group 6, Group 8, Group 9 and Group 10 of the periodic table on a support comprising porous inorganic oxides composed of substances selected from aluminum, silicon, zirconium, boron, titanium, magnesium and zeolite.

Examples of the porous inorganic oxide used as a support for such a hydroisomerization catalyst include alumina, titania, zirconia, boria, silica and zeolite, and, of these, those composed of alumina and at least one of titania, zirconia, boria, silica and zeolite are preferred. The production method thereof is not particularly limited and any preparation methods using a feedstock in the state of salt compounds or the like, a variety of sols compatible with respective element, can be employed. Additionally, a complex hydroxide or a complex oxides such as silica alumina, silica zirconia, alumina titania, silica titania, alumina boria, or the like, is prepared and then may be added for the preparation in the state of alumina gel, other hydroxides or a suitable solution at any step of the preparation method. The ratio of alumina to other oxides can be any ratio with respect to the support, and is preferably 90 mass % or less, further preferably 60 mass % or less, more preferably 40 mass % or less, preferably 10 mass % or more and more preferably 20 mass % or more, of alumina.

Zeolite is a crystalline aluminosilicate and examples thereof include faujasite, pentasil, mordenite, TON, MTT, *MRE, and the like, and those super-stabilized by a predetermined hydrothermal treatment and/or acid treatment or those containing an adjusted alumina content in zeolite can be used. Faujasite and mordenite are preferably used, and the Y-type and beta-type are particularly preferably used. The super-stabilized Y-type is preferred, and a zeolite super-stabilized by the hydrothermal treatment has new pores ranging from 20 to 100 Å formed, in addition to the intrinsic pore structure referred to as the micropore of 20 Å or less. The hydrothermal treatment can employ known conditions.

Examples of the active metal for such a hydroisomerization catalyst usable are at least one metal selected from the elements belonging to Group 6, Group 8, Group 9 and Group 10 of the periodic table. Of these metals, at least one metal selected from Pd, Pt, Rh, Ir and Ni is preferably used, and the combined use thereof is more preferred. Examples of the preferable combination include Pd—Pt, Pd—Ir, Pd—Rh, Pd—Ni, Pt—Rh, Pt—Ir, Pt—Ni, Rh—Ir, Rh—Ni, Ir—Ni, Pd—Pt—Rh, Pd—Pt—Ir, Pt—Pd—Ni, and the like. Of these, the combinations of Pd—Pt, Pd—Ni, Pt—Ni, Pd—Ir, Pt—Rh, Pt—Ir, Rh—Ir, Pd—Pt—Rh, Pd—Pt—Ni and Pd—Pt—Ir are more preferred, and the combinations of Pd—Pt, Pd—Ni, Pt—Ni, Pd—Ir, Pt—Ir, Pd—Pt—Ni and Pd—Pt—Ir are further preferred.

The total content of the active metals on a mass basis of the catalyst is, as a metal, preferably 0.1 to 2 mass %, more preferably 0.2 to 1.5 mass % and further preferably 0.5 to 1.3 mass %. When the total amount of supported metal is below 0.1 mass %, the active sites are reduced and the sufficient activity tends not to be obtained. Conversely, when such an amount exceeds 2 mass %, the metals are not effectively dispersed and the sufficient activity tends not to be obtained.

In any of the above hydroisomerization catalysts, the method for supporting the active metal on the support is not particularly limited, and the known method routinely applied to the hydroisomerization catalyst production can be used. Typically, the method in which a catalyst support is impregnated with a solution containing a salt of active metal is preferably employed. Equilibrium adsorption method, pore-filling method, incipient-wetness method, or the like, is also preferably employed. For example, pore-filling method is a method in which the pore volume of a support is measured in advance and the support is impregnated with a metal salt solution having the same volume as the measured volume, and the impregnation method is not particularly limited and the impregnation can be carried out by a suitable method according to the amount of metal supported and the physical properties of a catalyst support.

As hydroisomerization catalysts, the following catalysts can also be used. The hydroisomerization catalyst described in the following embodiment is not likely to suffer from the catalyst deactivation caused by changes in the isomerization dewaxing conditions, notably achieving the longer catalyst life performance which is the effect of the present invention.
<A Specific Embodiment of Hydroisomerization Catalyst>

The hydroisomerization catalyst of the present embodiment is imparted with the features thereof by a specific production process. Hereinafter, the hydroisomerization catalyst of the present embodiment is described with reference to preferred embodiments of the production thereof.

The method for producing a hydroisomerization catalyst of the present embodiment comprises a first step of obtaining a support precursor by heating at a temperature of 250 to 350° C. under an $N_2$ atmosphere a mixture containing a binder and an ion-exchanged zeolite obtained by ion-exchanging an organic template-containing zeolite containing an organic template and having a one-dimensional porous structure including a 10-membered ring in a solution containing ammonium ions and/or protons, and a second step of obtaining a hydroisomerization catalyst in which platinum and/or palladium is supported on a zeolite-containing support by calcining a catalyst precursor composed of the support precursor impregnated with platinum salt and/or palladium salt in an atmosphere containing molecular oxygen at a temperature of 350 to 400° C.

The organic template-containing zeolite used in the present embodiment has a one-dimensional pore structure made of a 10-membered ring, in view of achieving a high level of both high isomerization activity and suppressed cracking activity in the hydroisomerization reactions of normal paraffins. Examples of such zeolites include AEL, EUO, FER, HEU, MEL, MFI, NES, TON, MTT, WEI, *MRE and SSZ-32. It is noted that the above three alphabet letters designate framework-type codes assigned to various structures of classified molecular sieve-type zeolites by the Structure Commission of the International Zeolite Association. It is also noted that zeolites having the same topology are collectively designated by the same code.

Among the above-mentioned zeolites having a one-dimensional porous structure including a 10-membered ring, preferred as the organic template-containing zeolite are zeolites having the TON and MTT structures, zeolite ZSM-48 having the *MRE structure, and zeolite SSZ-32, in view of high isomerization activity and low cracking activity. Zeolite ZSM-22 is more preferred among zeolites having the TON structure, and zeolite ZSM-23 is more preferred among zeolites having the MTT structure.

The organic template-containing zeolite is hydrothermally synthesized according to a known method using a silica source, an alumina source, and an organic template that is added to construct the predetermined porous structure described above.

The organic template is an organic compound having an amino group, ammonium group, or the like, and is selected according to the structure of the zeolite to be synthesized; however, the organic template is preferably an amine derivative. Specifically, the organic template is preferably at least one selected from the group consisting of alkylamines, alkyldiamines, alkyltriamines, alkyltetramines, pyrrolidine, piperazine, aminopiperazine, alkylpentamines, alkylhexamines, and their derivatives. Typical examples of the alkyldiamines include 1,6-hexanediamine and 1,8-diaminooctane.

The molar ratio of the silicon element to aluminum element ([Si]/[Al]; hereinafter referred to as the "Si/Al ratio") that constitute the organic template-containing zeolite having a one-dimensional porous structure including a 10-membered ring is preferably 10 to 400, and more preferably 20 to 350. If the Si/Al ratio is less than 10, although the activity for the conversion of normal paraffins increases, the isomerization selectivity to isoparaffins tends to decrease, and cracking reactions tend to sharply increase as the reaction temperature increases, which is undesirable. Conversely, if the Si/Al ratio is more than 400, catalytic activity needed for the conversion of normal paraffins cannot be easily obtained, which is undesirable.

The synthesized organic template-containing zeolite, which has preferably been washed and dried, typically has alkali metal cations as counter cations, and incorporates the organic template in its porous structure. The zeolite containing an organic template, which is used for producing the hydroisomerization catalyst according to the present invention, is preferably in such a synthesized state, i.e., preferably, the zeolite has not been subjected to calcination treatment for removing the organic template incorporated therein.

The organic template-containing zeolite is subsequently ion-exchanged in a solution containing ammonium ions and/or protons. By the ion-exchange treatment, the counter cations contained in the organic template-containing zeolite are exchanged into ammonium ions and/or protons. At the same time, a portion of the organic template incorporated in the organic template-containing zeolite is removed.

The solution used for the ion-exchange treatment is preferably a solution that uses a solvent containing at least 50 vol % of water, and more preferably an aqueous solution. Examples of compounds for supplying ammonium ions into the solution include various inorganic and organic ammonium salts, such as ammonium chloride, ammonium sulfate, ammonium nitrate, ammonium phosphate, and ammonium acetate. On the other hand, mineral acids such as hydrochloric acid, sulfuric acid, and nitric acid are typically used as compounds for supplying protons into the solution. The ion-exchanged zeolite (herein, an ammonium-form zeolite) obtained by ion exchange of the organic template-containing zeolite in the presence of ammonium ions releases ammonia during subsequent calcination, and the counter cations are converted into protons to form Bronsted acid sites. Ammonium ions are preferred as the cationic species used for the ion exchange. The amount of ammonium ions and/or protons contained in the solution is preferably adjusted to 10 to 1000 equivalents relative to the total amount of the counter cations and organic template contained in the organic template-containing zeolite used.

The ion-exchange treatment may be applied to the organic template-containing zeolite support in powder form; alternatively, prior to the ion-exchange treatment, the organic template-containing zeolite may be mixed with an inorganic oxide, which is a binder, and extruded, and the ion-exchange treatment may be applied to the resulting extruded body. However, if the extruded body in its uncalcined state is subjected to the ion-exchanged treatment, the problem of collapsing and powdering of the extruded body will easily arise; therefore, it is preferred to subject the organic template-containing zeolite in powder form to the ion-exchange treatment.

The ion-exchange treatment is preferably performed according to a standard method, i.e., a method in which the organic template-containing zeolite is immersed in a solution, preferably an aqueous solution, containing ammonium ions and/or protons, and the solution is stirred and fluidized. The stirring or fluidization is preferably performed under heating to improve the ion-exchange efficiency. In the present embodiment, it is particularly preferred to use a method in which the aqueous solution is heated, boiled, and ion-exchanged under reflux.

Further, in view of improving the ion-exchange efficiency, during the ion exchange of the zeolite in a solution, the solution is preferably exchanged with a fresh one once or twice or more, and more preferably exchanged with a fresh one once or twice. When the solution is exchanged once, the ion-exchange efficiency can be improved by, for example, immersing the organic template-containing zeolite in a solution containing ammonium ions and/or protons, and heating the solution under reflux for 1 to 6 hours, followed by exchanging the solution with a fresh one, and further heating under reflux for 6 to 12 hours.

By the ion-exchange treatment, substantially all of the counter cations such as an alkali metal in the zeolite can be exchanged into ammonium ions and/or protons. On the other hand, with respect to the organic template incorporated in the zeolite, although a portion of the organic template is removed by the ion-exchange treatment, it is generally difficult to remove all of the organic template even if the ion-exchange treatment is repeatedly performed, resulting in a portion of the organic template remaining inside the zeolite.

In the present embodiment, a mixture containing an ion-exchanged zeolite and a binder is heated under a nitrogen atmosphere at a temperature of 250 to 350° C. to obtain a support precursor.

In a mixture containing an ion-exchanged zeolite and a binder, it is preferred to mix the ion-exchanged zeolite obtained by the above-described method with an inorganic oxide, which is a binder, and extrude the resulting composition. The purpose of mixing the ion-exchanged zeolite with an inorganic oxide is to increase the mechanical strength of the support (in particular, a particulate support) obtained by calcining the extruded body to a degree that can withstand practical applications; however, the present inventors have found that the selection of the type of inorganic oxide affects the isomerization selectivity of the hydroisomerization catalyst. From this viewpoint, at least one inorganic oxide selected from alumina, silica, titania, boria, zirconia, magnesia, ceria, zinc oxide, phosphorus oxide, and a composite oxide containing a combination of at least two or more of these oxides can be used as the inorganic oxide. Among the above, silica and alumina are preferred in view of further improving the isomerization selectivity of the hydroisomerization catalyst, and alumina is more preferred. The phrase "composite oxide containing a combination of at least two or more of these oxides" is a composite oxide containing at least two components from alumina, silica, titania, boria, zirconia, magnesia, ceria, zinc oxide, and phosphorus oxide, but is preferably an alumina-based composite oxide containing 50 mass % or more of an alumina component based on the composite oxide, and more preferably an alumina-silica.

The proportion of the ion-exchanged zeolite to the inorganic oxide in the above-mentioned composition is preferably 10:90 to 90:10, and more preferably 30:70 to 85:15, in terms of the mass ratio of the ion-exchanged zeolite to the inorganic oxide. If this ratio is less than 10:90, the activity of the hydroisomerization catalyst tends to be insufficient, which is undesirable. Conversely, if the ratio is more than 90:10, the mechanical strength of the support obtained by extruding and calcining the composition tends to be insufficient, which is undesirable.

Although the method for mixing the ion-exchanged zeolite with the inorganic oxide is not particularly limited, a general method can be employed, such as, for example, a method in which a suitable amount of a liquid such as water is added to the powders of both components to form a viscous fluid, and the fluid is kneaded in a kneader or the like.

The composition containing the ion-exchanged zeolite and inorganic oxide, or a viscous fluid containing the composition, is extruded by extrusion or other methods, and is preferably dried, to form a particulate extruded body. Although the shape of the extruded body is not particularly limited, the extruded body may, for example, have a cylindrical shape, pellet shape, spherical shape, or irregular tubular shape having a three leaf-shaped or four leaf-shaped cross section. Although the size of the extruded body is not particularly limited, the extruded body is preferably, for example, about 1 to 30 mm in long axis, and about 1 to 20 mm in short axis, in view of the ease of handling, the load density in the reactor, etc.

In the present embodiment, it is preferred that the extruded body thus obtained as described above is heated under an $N_2$ atmosphere at the lower limit of 250° C. or higher, more preferably 280° C. or higher, and at the upper limit of 350° C. or lower, more preferably 330° C. or lower to prepare a support precursor. The heating time is preferably 0.5 to 10 hours, more preferably 1 to 5 hours.

In the present embodiment, when the above heating temperature is lower than 250° C., the organic template remains in a large amount and the residual template blocks the zeolite pores. The isomerization active sites are believed to be near the pore mouth, and, in the above case, the reaction substrates are failed to disperse into the pores due to the pore blockage, the blocked active sites hinder the progress of isomerization reaction, and the sufficient normal paraffin conversion tends not to be achieved. On the other hand, when the heating temperature exceeds 350° C., the isomerization selectivity of the resulting hydroisomerization catalyst does not improve sufficiently.

The lower limit temperature at the time of heating the extruded body to prepare the support precursor is preferably 280° C. or higher. The upper limit temperature is preferably 330° C. or lower.

In the present embodiment, the above mixture is preferably heated so as a part of the organic template contained in the above extruded body to remain. Specifically, it is preferred to set the heating conditions so that the carbon content of the hydroisomerization catalyst obtained by calcination after metal supporting, which will be described below, is 0.4 to 3.5% by mass (preferably 0.4 to 3.0% by mass, more preferably 0.4 to 2.5% by mass), or the micropore volume per unit mass of the hydroisomerization catalyst obtained by calcination after metal supporting is 0.02 to 0.12 cc/g and the micropore volume per unit mass of the zeolite contained in the catalyst is 0.01 to 0.12 cc/g.

Subsequently, the catalyst precursor composed of the above support precursor impregnated with a platinum salt and/or palladium salt is calcined in an atmosphere containing molecular oxygen at a temperature of 350 to 400° C., preferably 380 to 400° C., more preferably 400° C., to obtain a hydroisomerization catalyst in which platinum and/or palladium is supported on the zeolite-containing support. The term "in an atmosphere containing molecular oxygen" means contacting with gases containing oxygen gas, and, particularly preferably with air. The calcination time is preferably 0.5 to 10 hours, more preferably 1 to 5 hours.

Examples of the platinum salt include chloroplatinic acid, tetraammine dinitro platinum, dinitro aminoplatinum, tetraammine dichloroplatinum, and the like. Chloride salts may cause the device corrosion by the hydrochloric acid produced during the reaction and it is thus preferred to use tetraammine dinitro platinum, that is a platinum salt in which platinum is highly dispersible other than chloride salts.

Examples of the palladium salt include palladium chloride, tetraammine palladium nitrate, diaminopalladium nitrate, and the like. Chloride salts may cause the device corrosion by the hydrochloric acid produced during the reaction and it is thus preferred to use tetraammine palladium nitrate, that is a palladium salt in which palladium is highly dispersible other than chloride salts.

The amount of the active metal supported on the support containing the zeolite of the present embodiment is preferably 0.001 to 20 mass %, more preferably 0.01 to 5 mass %, based on the mass of the support. When an amount of the supported metal is below 0.001 mass %, it will be difficult to impart a predetermined hydrogenation/dehydrogenation function. Conversely, when an amount of the supported metal exceeds 20 mass %, the conversion of hydrocarbons into lighter products on the active metal by cracking tends to easily proceed, causing a tendency to decrease the yield of a desired fraction, and further causing a tendency to increase the catalyst costs, which is undesirable.

Moreover, when the hydroisomerization catalyst of the present embodiment is used for the hydrogenation isomerization of a hydrocarbon oil containing many sulfur-containing compounds and/or nitrogen-containing compounds, it is preferred that the hydroisomerization catalyst contains, as active metals, a combination such as Ni-cobalt, Ni-molybdenum, cobalt-molybdenum, Ni-molybdenum-cobalt, Ni-tungsten-cobalt, or the like, in view of the durability of catalytic activity. The amount of these metals supported is preferably 0.001 to 50 mass %, more preferably 0.01 to 30 mass %, based on the mass of the support.

In the present embodiment, it is preferred to calcine the above catalyst precursor so as the residual organic template in the above support precursor to remain. Specifically, it is preferred to set the heating conditions so that the carbon content of the obtained hydroisomerization catalyst is 0.4 to 3.0% by mass (preferably 0.4 to 3.0% by mass, more preferably 0.4 to 2.5% by mass), or the micropore volume per unit mass of the obtained hydroisomerization catalyst is 0.02 to 0.12 cc/g and the micropore volume per unit mass of the zeolite contained in the catalyst is 0.01 to 0.12 cc/g. The carbon content of the hydroisomerization catalyst is measured by "combustion in oxygen gas flow–infrared absorption method". Specifically, the catalyst is combusted in the oxygen gas flow to generate carbon dioxide gas and the carbon content is determined based on an infrared absorption amount of the carbon dioxide gas. Analysis equipments for carbon-sulfur (for example, EMIA-920V manufactured by HORIBA, Ltd.) are used for the measurement.

The micropore volume per unit mass of the hydroisomerization catalyst is calculated by the method called the nitrogen adsorption measurement. In other words, the micropore volume per unit mass of the catalyst is calculated by analyzing the nitrogen physical adsorption-desorption isotherm of the catalyst measured at the liquid nitrogen temperature (−196° C.), specifically, by analyzing the nitrogen adsorption isotherm measured at the liquid nitrogen temperature (−196° C.) using the t-plot method. The micropore volume per unit mass of the zeolite contained in the catalyst can also be calculated by the above nitrogen adsorption measurement.

The micropore volume per unit mass of the zeolite contained in the catalyst $V_Z$ can be calculated, for example, when the binder does not have a micropore volume, by the following formula based on the value of micropore volume per unit mass of the hydroisomerization catalyst $V_c$ and the content ratio of the zeolite in the catalyst $M_z$ (mass %).

$$V_Z = V_c/M_z \times 100$$

It is preferred for the hydroisomerization catalyst of the present embodiment to be those, subsequent to the above calcination treatment, subjected to reduction treatment after loaded in a reactor in which the hydroisomerization reaction is carried out. Specifically, it is preferred that the catalyst be those subjected to the reduction treatment performed for about 0.5 to 5 hours in an atmosphere containing molecular hydrogen, preferably under a stream of hydrogen gas, preferably at 250 to 500° C., and more preferably at 300 to 400° C. Such a step further ensures that the catalyst can be provided with high activity on dewaxing of a hydrocarbon oil.

The hydroisomerization catalyst of the present embodiment can also be said to be a hydroisomerization catalyst which contains a zeolite having a one-dimensional porous structure including a 10-membered ring, a support containing a binder, and platinum and/or palladium supported on the support, wherein the catalyst has a carbon content of 0.4 to 3.5% by mass and the micropore volume per unit mass of the catalyst of 0.02 to 0.12 cc/g, wherein the zeolite is derived from an ion-exchanged zeolite obtained by ion-exchanging an organic template-containing zeolite containing an organic template and having a one-dimensional porous structure including a 10-membered ring in a solution containing ammonium ions and/or protons and the micropore volume per unit mass of the zeolite contained in the catalyst is 0.01 to 0.12 cc/g.

The above hydroisomerization catalyst can be produced by the method mentioned above. The carbon content of the catalyst, the micropore volume per unit mass of the catalyst and the micropore volume per unit mass of the zeolite contained in the catalyst can be adjusted to be within the above range by suitably adjusting the amount of ion-exchanged zeolite added to the mixture containing the ion-exchanged zeolite and binder, the heating conditions for the mixture under an $N_2$ atmosphere and the heating conditions for the catalyst precursor under an atmosphere containing molecular oxygen.

Additionally, in the present specification, the micropore volume per unit mass of the hydroisomerization catalyst is calculated by the method called the nitrogen adsorption measurement. In other words, the micropore volume per unit mass of the catalyst is calculated by analyzing the nitrogen physical adsorption-desorption isotherm of the catalyst measured at the liquid nitrogen temperature (−196° C.), specifically, by analyzing the nitrogen adsorption isotherm measured at the liquid nitrogen temperature (−196° C.) using the t-plot method. The micropore volume per unit mass of the zeolite contained in the catalyst is also calculated by the above nitrogen adsorption measurement.

Further, the micropore used in the present specification means the "pore having a diameter of 2 nm or less" as designated by IUPAC (International Union of Pure and Applied Chemistry).

In the isomerization dewaxing of the first step, a part or whole of the normal paraffin contained in a hydrocarbon oil is converted to isoparaffin by the hydroisomerization reaction.

In the isomerization dewaxing of the first step, it is preferred that the hydrocarbon oil and hydroisomerization catalyst be contacted with each other under conditions such that the conversion of the normal paraffin as defined by the following formula (I) is substantially 100 mass %.

[Expression 1]

$$\text{Conversion of normal paraffins}(\%) = \left[1 - \frac{\left(\begin{array}{c}\text{Total mass \% of normal paraffins having}\\ \text{Cn or more carbon atoms contained}\\ \text{in a hydrocarbon oil after the contact}\end{array}\right)}{\left(\begin{array}{c}\text{Total mass \% of normal paraffins having}\\ \text{Cn or more carbon atoms contained}\\ \text{in the hydrocarbon oil before the contact}\end{array}\right)}\right] \times 100 \quad (1)$$

In the formula (I), Cn represents the minimum number of carbon atoms of the normal paraffins having 10 or more carbon atoms contained in the hydrocarbon oil (feedstock) before the contact.

The phrase "substantially 100 mass % conversion" means that the amount of normal paraffins contained in the hydrocarbon oil after the contact is 0.1 mass % or less.

The hydrocarbon oil subjected to the first step is not particularly limited insofar as it contains normal paraffins having a boiling point of 360° C. or higher but preferably petroleum fractions, synthetic oils and waxes, and the like, that are fractions having a boiling point of more than 360° C. as calculated at atmospheric pressure. Specific examples of hydrocarbon oil include heavy gas oils, vacuum gas oils, lubricant oil raffinates, brightstocks, slack waxes (crude waxes), foot's oils, deoiled waxes, paraffinic waxes, microcrystalline waxes, petrolatum, synthetic oils, FT synthesis oils, FT synthesis wax, high-pour-point polyolefins, and straight-chain α-olefin waxes. It is particularly preferred to use atmospheric residual oils, vacuum gas oils, vacuum residual oils, slack waxes, FT synthesis oils and FT synthesis waxes. They can be used singly or in combinations of two or more. Further, these hydrocarbon oils are preferably hydroprocessed or lightly hydrocracked. These treatments can reduce or remove sulfur-containing compounds, nitrogen-containing compounds, and other substances that cause the activity of the hydroisomerization catalyst to decrease, and aromatic hydrocarbons, naphthenic hydrocarbons, and other substances that cause the viscosity index of the lubricant base oil to decrease.

The contact of such a hydrocarbon oil with the hydroisomerization catalyst in the presence of hydrogen allows the isomerization of the normal paraffins contained in the hydrocarbon oil, i.e., the dewaxing reaction of the hydrocarbon oil, to proceed, while sufficiently suppressing the conversion of the hydrocarbon oil into lighter products. According to the first step of the present embodiment, a base oil containing many branched-chain isomers can be obtained. In particular, a high-quality lubricant base oil is required to have a normal paraffin content of 0.1 mass % or less; and according to the production method of the present embodiment, a lubricant base oil that meets this level of the requirement can be produced in high yield.

The reaction temperature of the isomerization dewaxing in the first step is preferably 200 to 450° C., and more preferably 300 to 430° C. If the reaction temperature is below 200° C., the isomerization of the normal paraffins contained in the feedstock oil tends not to easily proceed, resulting in insufficient reduction and removal of the waxy components. Conversely, if the reaction temperature is more than 450° C., cracking of the hydrocarbon oil tends to be significant, resulting in a reduced yield of a desired hydrocarbon.

The reaction pressure in the isomerization dewaxing is preferably 0.1 to 20 MPa, and more preferably 0.5 to 18 MPa. If the reaction pressure is below 0.1 MPa, catalyst deterioration due to the formation of coke tends to be accelerated. Conversely, if the reaction pressure is more than 20 MPa, construction costs for the apparatus tend to increase, making it difficult to realize an economic process.

The liquid hourly space velocity (LHSV) of the hydrocarbon oil relative to the catalyst is preferably 0.01 to 100 $h^{-1}$, and more preferably 0.1 to 10 $h^{-1}$. If the liquid hourly space velocity is less than 0.01 $h^{-1}$, excessive cracking of the hydrocarbon oil tends to easily proceed, resulting in lowered production efficiency for a desired lubricant base oil. Conversely, if the liquid hourly space velocity is more than 100 $h^{-1}$, the isomerization of the normal paraffins contained in the hydrocarbon oil tends not to easily proceed, resulting in insufficient reduction and removal of the waxy components.

The feed ratio of hydrogen to feedstock oil (hydrogen/oil ratio) is preferably 100 to 1000 Nm$^3$/m$^3$, and more preferably 200 to 800 Nm$^3$/m$^3$. If the feed ratio is less than 100 Nm$^3$/m$^3$, for example, when the hydrocarbon oil contains sulfur and nitrogen compounds, hydrogen sulfide and ammonia gas produced by hydrodesulfurization and hydrodenitrification reactions that accompany the isomerization reaction tend to adsorb onto and poison the active metal on the catalyst, thus making it difficult to achieve predetermined catalytic performance. Conversely, if the feed ratio is more than 1000 Nm$^3$/m$^3$, hydrogen feed equipment having increased capacity tends to be required, making it difficult to realize an economical process.

In the first step, the normal paraffin conversion can be typically increased by, for example, raising the reaction temperature, and the normal paraffin content in the resulting dewaxed oil can be reduced, thereby improving the cold flow property of the hydrocarbon oil. However, an increased reaction temperature promotes the cracking reactions of the hydrocarbon oil feedstock and isomerized products, thereby increasing cracking rate as the normal paraffin conversion is increased. In the first step, it is necessary to carry out the isomerization dewaxing under conditions such that the cracking rate is 10 mass % or less.

The method for producing a lubricant base oil according to the present embodiment is not particularly limited, and known equipment can be employed. The reaction equipment may be any of a continuous flow-type, a batch-type, and a semi-batch-type; however, a continuous flow-type is preferred in view of productivity and efficiency. The catalyst bed may be any of a fixed bed, a fluidized bed, and a stirred bed; however, a fixed bed is preferred in view of equipment costs and the like. The reaction phase is preferably a mixed phase of gas and liquid.

In the method for producing a lubricant base oil according to the present embodiment, the hydrocarbon oil as a feedstock to be fed may be hydroprocessed or hydrocracked as a stage prior to the first step. Known equipment, catalysts, and reaction conditions can be used for the hydroprocessing or hydrocracking. By carrying out these pre-treatments, it is possible to maintain the activity of the hydroisomerization catalyst over an extended period of time, and to reduce the amount of substances of concern such as sulfur- and nitrogen-containing compounds in the product.

(Second Step)

In the second step (hereinafter in some cases referred to as "cracking treatment step"), the isomerization dewaxing conditions in the first step are temporarily switched to conditions such that the cracking rate is 13 mass % or more.

According to the findings by the present inventors, when isomerically dewaxing a hydrocarbon oil containing normal paraffin having a boiling point of 360° C. or higher, a cause of the low activation of a hydroisomerization catalyst is the drift of a hydrocarbon oil. Thus, in the production method of the present embodiment, while the isomerization dewaxing is carried out with the sufficiently suppressed hydrocarbon oil cracking in the first step, the drift caused in the first step is eliminated by the temporarily performed second step, thereby achieving the longer catalyst life performance.

More specifically, according to the production method of the present embodiment, when the isomerization dewaxing is carried out under conditions such that intentionally the cracking rate is 13 mass % or more in the second step, a low viscous hydrocarbon oil having high flow property is produced in the isomerization dewaxing reactor and the circulation of this low viscous hydrocarbon oil in the isomerization dewaxing reactor eliminates the above drift.

In the second step, the cracking rate can be adjusted to 13 mass % or more by changing the reaction temperature, LHSV, reaction pressure, and the like, from the isomerization dewaxing conditions of the first step.

In the second step, the cracking rate can be raised, for example, by increasing the reaction temperature of the isomerization dewaxing conditions. The cracking rate can also be raised by reducing the liquid hourly space velocity (LHSV) with respect to the catalyst for a hydrocarbon oil (that is, the contact time of the hydrocarbon oil and the catalyst is extended). Further, the cracking rate can be raised by increasing the reaction pressure.

Of these, LHSV and the reaction pressure have limited variable ranges depending on the size, and the like, of the reactor, and it is hence preferred that the cracking rate be adjusted to 13 mass % or more by increasing the reaction temperature in the second step. Further, in the second step, any one of the isomerization dewaxing conditions (e.g., reaction temperature) used in the first step may be changed to give the cracking rate of 13 mass % or more, or a plurality of conditions may be changed to give the cracking rate of 13 mass % or more.

The isomerization dewaxing conditions in the second step is preferably those so as to give a cracking rate of 13 to 50 mass %, more preferably those so as to give a cracking rate of 15 to 30 mass %. The effect of the present invention is more remarkably achieved when the isomerization dewaxing of the second step is carried out with such a cracking rate.

According to the production method of the present embodiment, after temporarily carrying out the second step, the isomerization dewaxing conditions can be returned to conditions such that the cracking rate is 10 mass % or less to carry out the first step. Preferably, while carrying out the first step continuously, the second step can be carried out at the predetermined intervals. More specifically, according to the production method of the present embodiment, the first step and the second step can alternately be carried out in a repetitive manner.

The processing time of the second step can be suitably changed according to the size, or the like, of a reactor to be used and, for example, can be 1 to 120 hours. Further, the second step can be carried out after the first step is carried out for, for example, preferably 5 hours, more preferably 12 hours or longer and 90 days or less.

The proceeding ratio of the first step to the second step can be defined by the ratio of hydrocarbon oils subjected to each step. The first step and the second step are preferably carried out respectively so that the ratio of the hydrocarbon oil B subjected to the second step to the hydrocarbon oil A subjected to the first step B/A is 0.01 to 1, more preferably the ratio B/A is 0.1 to 0.5.

(Other Step)

In the method for producing a lubricant base oil according to the present embodiment, the reaction product (dewaxed oil) obtained by isomerization dewaxing in which a hydrocarbon oil is contacted with the hydroisomerization catalyst can further be treated by, for example, hydrofinishing. Hydrofinishing can be typically carried out by contacting, in the presence of hydrogen, a hydrogenation catalyst supported on a metal (e.g., platinum and/or palladium supported on alumina), with the product to be finished. By performing such hydrofinishing, it is possible to improve the hue, oxidation stability, and the like of the reaction product obtained in the dewaxing step (first and second steps), thereby enhancing the product quality. The hydrofinishing may be carried out in reaction equipment separate from that of the dewaxing step; alternatively, a catalyst layer for hydrofinishing may be provided downstream the catalyst layer of the hydroisomerization catalyst provided in the reactor for performing the dewaxing step, and the hydrofinishing may be performed subsequent to the dewaxing step. The hydrofinishing may be referred to as a hydrorefining and hereinafter, the hydrofinishing step is referred to as a hydrorefining step.

Further, the method for producing a lubricant base oil of the present embodiment may further comprise a distillation step in which a base oil fraction having a predetermined boiling point range is fractionated.

For example, the method for producing a lubricant base oil of the present embodiment may further comprise a hydrorefining step for obtaining a hydrorefined oil by hydrorefining the dewaxed oil obtained in the first step and the second step, and a distillation step for fractionating a base oil fraction from the hydrorefined oil obtained in the hydrorefining step. Further, the method for producing a lubricant base oil of the present embodiment may furthermore comprise a distillation step for fractionating a base oil fraction from the dewaxed oil obtained in the first step and the second step, and a hydrorefining step for hydrorefining the base oil fraction fractionated in the distillation step.

It is noted that, in general, isomerization refers to a reaction whereby only the molecular structure changes without a change in the number of carbon atoms (the molecular weight), and cracking refers to a reaction that involves a decrease in the number of carbon atoms (molecular weight). In the isomerization dewaxing utilizing the isomerization reaction, a certain degree of cracking of the hydrocarbon oil used as a stock and isomerized products may occur, as long as the number of carbon atoms (the molecular weight) of the product is maintained within a predetermined range that permits the formation of an intended base oil, and the cracked products may also be constituents of the base oil.

Hereinabove, the preferred embodiments of the present invention have been described but the present invention is not limited thereto.

EXAMPLES

The present invention will be described in more detail below, referring to examples; however, the invention is not limited to these examples.

Production Example 1: Production of Hydroisomerization Catalysts E-1

<Production of a Zeolite ZSM-22>

A zeolite ZSM-22 (hereinafter sometimes referred to as the "ZSM-22") made of a crystalline aluminosilicate having a Si/Al ratio of 45 was produced by hydrothermal synthesis.

First, the following four types of aqueous solutions were prepared.
Solution A: A solution prepared by dissolving 1.94 g of potassium hydroxide in 6.75 mL of ion-exchange water.
Solution B: A solution prepared by dissolving 1.33 g of aluminum sulfate 18-hydrate in 5 mL of ion-exchange water.
Solution C: A solution prepared by diluting 4.18 g of 1,6-hexanediamine (an organic template) with 32.5 mL of ion-exchange water.
Solution D: A solution prepared by diluting 18 g of colloidal silica (Ludox AS-40 by Grace Davison) with 31 mL of ion-exchange water.

Next, Solution A was added to Solution B, and the mixture was stirred until the aluminum component completely dissolved.

After Solution C was added to this mixed solution, the mixture of Solutions A, B, and C was poured into Solution D with vigorous stirring at room temperature. To the resulting mixture was further added, as a "seed crystal" that promotes crystallization, 0.25 g of a powder of ZSM-22 that had been separately synthesized, and had not been subjected to any special treatment after the synthesis, thereby giving a gel.

The gel obtained by the above procedure was transferred into a 120 mL internal volume stainless steel autoclave reactor, and the autoclave reactor was rotated at a rotational speed of about 60 rpm on a tumbling apparatus for 60 hours in an oven at 150° C., causing a hydrothermal synthesis reaction to take place. After the completion of the reaction, the reactor was opened after cooling, and dried overnight in a drier at 60° C., thereby giving ZSM-22 having a Si/Al ratio of 45.

<Ion Exchange of Organic Template-Containing ZSM-22>

The ZSM-22 obtained above was subjected to ion-exchange treatment in an aqueous solution containing ammonium ions, according to the following procedure.

The ZSM-22 obtained above was taken in a flask, and 100 mL of 0.5 N-ammonium chloride aqueous solution per gram of the zeolite ZSM-22 was added thereto, and the mixture was heated under reflux for 6 hours. After cooling the heated mixture to room temperature, the supernatant was removed, and the crystalline aluminosilicate was washed with ion-exchange water. To the resulting product, the same amount of 0.5 N-ammonium chloride aqueous solution as above was added again, and the mixture was heated under reflux for 12 hours.

Subsequently, the solids were extracted by filtration, washed with ion-exchanged water, and dried overnight in a drier at 60° C., thereby giving ion-exchanged, $NH_4$-form ZSM-22. The ZSM-22 was an ion-exchanged zeolite containing an organic template.

<Mixing of a Binder, Extruding, and Calcination>

The $NH_4$-form ZSM-22 obtained above was mixed with alumina, i.e., a binder, in a mass ratio of 7:3, a small amount of ion-exchange water was added thereto, and the mixture was kneaded. The resulting viscous fluid was loaded in an extruder and extruded into a cylindrical extruded body having a diameter of about 1.6 mm and a length of about 10 mm. This extruded body was heated under $N_2$ atmosphere for 3 hours at 300° C., thereby giving support precursor.

<Supporting of Platinum and Palladium, and Calcination>

Tetraamminedinitroplatinum (II) $[Pt(NH_3)_4](NO_3)_2$ and tetraamminepalladium nitrate $[Pd(NH_3)_4](NO_3)_2$ was dissolved in an amount of ion-exchange water equivalent to the amount of water absorption of the support precursor that had been previously measured, thus giving an impregnation solution. This solution was impregnated in the above-described support precursor by incipient wetting, and supported on the support precursor such that the amount of platinum and the amount of palladium were 0.3 mass % each based on the mass of the zeolite ZSM-22. Next, the resulting impregnation product (catalyst precursor) was dried overnight in a drier at 60° C., and then calcined under an air stream for 3 hours at 400° C., thereby giving Hydroisomerization Catalyst E-1.

Further, the micropore volume per unit mass of the resulting hydroisomerization catalyst was calculated by the following method. To remove the moisture adsorbed to the hydroisomerization catalyst, the pretreatment of vacuum pumping was first carried out at 150° C. for 5 hours. The pretreated hydroisomerization catalyst was subjected to the nitrogen adsorption measurement at the liquid nitrogen temperature (−196° C.) using a BELSORP-max manufactured by BEL Japan, Inc. The measured nitrogen adsorption isotherm was analyzed by the t-plot method to calculate the micropore volume per unit mass (cc/g) of the hydroisomerization catalyst containing 0.56% by mass of carbon. The carbon content of the catalyst was measured by "combustion in oxygen gas flow–infrared absorption method". EMIA-920V manufactured by HORIBA, Ltd. was used for the measurement.

The micropore volume per unit mass of the zeolite contained in the catalyst $V_Z$ was calculated by the following formula. Additionally, the alumina used as the binder was similarly subjected to the nitrogen adsorption measurement and was confirmed not to have a micropore.

$$V_Z = V_c/M_z \times 100$$

In the formula, $V_c$ represents the micropore volume per unit mass of the hydroisomerization catalyst, and $M_z$ represents the content ratio (mass %) of the zeolite contained in the catalyst.

Production Example 2: Production of Hydroisomerization Catalysts E-2

<Production of a Zeolite ZSM-48>

An organic template-containing zeolite ZSM-48 (hereinafter sometimes referred to as the "ZSM-48") having a Si/Al ratio of 45 was hydrothermally synthesized by the following procedure.

First, the following four types of reagents were prepared.
Reagent E: 2.97 g of sodium hydroxide.
Reagent F: 0.80 g of aluminum sulfate 18-hydrate.
Reagent G: 26.2 g of 1,6-hexanediamine (organic template).
Reagent H: 0.9 ml of a 98% sulfuric acid solution.
Reagent I: 75 g of a colloidal silica (Ludox AS-40 by Grace Davison) aqueous solution ($SiO_2$ concentration 40%).

Next, Reagents E, F, G, H, and I mentioned above were added to 180 mg of ion-exchange water, and then completely dissolved by stirring for 2 hours at room temperature.

The gel obtained by above procedure was transferred into a 100 mL internal volume stainless steel autoclave reactor, and the autoclave reactor was rotated at a rotational speed of about 60 rpm on a tumbling apparatus for 60 hours in an oven at 160° C., causing a hydrothermal synthesis reaction to take place. After the completion of the reaction, the reactor was opened after cooling, and dried overnight in a drier at 60° C., thereby giving ZSM-48 having a Si/Al ratio of 45.

<Ion Exchange of Organic Template-Containing ZSM-48>

The same procedure as the ion exchange of ZSM-22 in Example 1 was performed, except that the organic template-containing ZSM-48 obtained above was used instead of the organic template-containing ZSM-22, thereby giving ion-exchanged NIL-form ZSM-48.

The production and heating of the extruded body as well as the preparation and calcination of the catalyst precursor were carried out in the same procedure as Production Example 1, except that the obtained $NH_4$-form ZSM-48 was used in place of $NH_4$-form ZSM-22, thereby obtaining a hydroisomerization catalyst E-2 containing 0.43% by mass of carbon.

Production Example 3: Production of Hydroisomerization Catalyst E-3

<Production of SSZ-32 Zeolite>

SSZ-32 Zeolite (hereinafter sometimes referred to as "SSZ-32") was hydrothermally synthesized by the following procedure according to the method described in Japanese Examined Patent Publication No. 2006-523136.

A mixture of sodium hydroxide, aluminum sulfate, colloidal silica, isobutylamine and N-methyl-N-isopropyl-imidazorium cation was prepared in the following molar ratio. $SiO_2/Al_2O_3=35$, the total amount of isobutylamine and N-methyl-N'-isopropyl-imidazolium cation was 0.2 times that of $SiO_2$.

The gel obtained by the above procedure was transferred into a 100 mL internal volume stainless steel autoclave reactor, and the autoclave reactor was rotated at a rotational speed of about 60 rpm on a tumbling apparatus for 60 hours in an oven at 160° C., causing a hydrothermal synthesis reaction to take place. After completion of the reaction, the reactor was opened after cooling, and the product was dried overnight in a drier at 60° C., thereby giving SSZ-32 having an Si/Al ratio of 45.

<Ion Exchange of Organic Template-Containing SSZ-32>

The same procedure as the ion exchange of ZSM-22 in Production Example 1 was carried out, except that the obtained organic template-containing SSZ-32 was used instead of the organic template-containing ZSM-22, thereby obtaining an ion-exchanged $NH_4$-form SSZ-32.

The production and heating of the extruded body as well as the preparation and calcination of the catalyst precursor were carried out in the same procedure as Production Example 1, except that the obtained $NH_4$-form SSZ-32 was used in place of $NH_4$-form ZSM-22, thereby obtaining a hydroisomerization catalyst E-3 containing 0.50% by mass of carbon.

TABLE 1

| | Zeolite | Heating conditions of extruded body | | Calcination conditions of catalyst precursor | | Micropore volume per unit mass of catalyst (cc/g) | Micropore volume per unit mass of zeolite contained in catalyst (cc/g) | Active metal | Carbon content in catalyst (% by mass) |
|---|---|---|---|---|---|---|---|---|---|
| | | Atmosphere | Temperature (° C.) | Atmosphere | Temperature (° C.) | | | | |
| Production Example 1 | ZSM-22 | $N_2$ | 300 | Air | 400 | 0.055 | 0.079 | Pt, Pd | 0.56 |
| Production Example 2 | ZSM-48 | $N_2$ | 300 | Air | 400 | 0.078 | 0.111 | Pt, Pd | 0.43 |
| Production Example 3 | SSZ-32 | $N_2$ | 300 | Air | 400 | 0.062 | 0.089 | Pt, Pd | 0.50 |

Example 1

First Step (Isomerization Treatment Step)

Catalyst E-1 was used as the isomerization dewaxing catalyst. A stainless-steel reaction tube having an inner diameter of 15 mm and a length of 380 mm was loaded with 100 ml of the extruded catalyst, and reduction treatment was carried out for 12 hours under a hydrogen stream (the hydrogen partial pressure: 3 MPa) at a catalyst layer average temperature of 350° C. Subsequently, a hydrocarbon oil (a vacuum gas oil faction having a boiling point range from 150 to 650° C. and a sulfur content of 30 mass ppm) obtained by desulfuring the vacuum gas oil was passed through the reaction tube under conditions of a reaction temperature of 310 to 350° C., a hydrogen partial pressure of 11 MPa, a LHSV of 1.0 $h^{-1}$, and a hydrogen/oil ratio of 500 NL/L, and the dewaxing treatment by hydroisomerization reaction was carried out. The reaction temperature was initially set at the reaction initial temperature Tc (° C.) as described below and increased stepwise to give a normal paraffin conversion of 100%. The initial cracking rate in the first step was 4 mass %.

<Separation and Recovery of Lubricant Base Oil Fractions>

The reaction product obtained in the isomerization treatment step was fractionated by the following procedure, and the lubricant base oil fraction was separated and recovered. The pour point and viscosity index of the recovered lubricant base oil fraction were measured to determine the temperature at which the isomerization dewaxing sufficiently proceeds in the initial stage of the reaction (reaction initial temperature Tc (° C.)).

Specifically, the reaction product was first fractionated into naphtha, kerosene and gas oil fractions, and heavy fractions, respectively. Further, a lubricant base oil fraction having a boiling point range of 410 to 450° C. and a kinematic viscosity at 100° C. of 4.0±0.1 $mm^2/s$ (hereinafter referred to as the "lubricant base oil fraction 1"), a lubricant base oil fraction having a boiling point range of 450 to 520° C. and a kinematic viscosity at 100° C. of 7.0±0.1 $mm^2/s$ (hereinafter referred to as the "lubricant base oil fraction 2"), and a lubricant base oil fraction having a boiling point range of 520° C. or higher and a kinematic viscosity at 100° C. of 10.5±0.1 $mm^2/s$ (hereinafter referred to as the "lubricant base oil fraction 3") were obtained. Tc (° C.) was defined as the lowest reaction initial temperature at which the reaction product has a normal paraffin conversion of 100% as well as the lubricant base oil fraction 3 has a pour point of −12.5° C. or lower and a viscosity index of 105 or higher.

Second Step (Cracking Treatment Step)

After the above first step, the reaction temperature was increased to a temperature at which the cracking rate was 30 mass % (372° C.) with the hydrogen partial pressure, LHSV and hydrogen/oil ratio remained unchanged, and the temperature was maintained for 24 hours to carry out the cracking treatment step. In the cracking treatment step, the reaction product was analyzed by gas chromatography to understand the cracking rate at each reaction temperature, thereby selecting the reaction temperature at which a predetermined cracking rate was attained.

After the cracking treatment step, the reaction temperature was reduced to the temperature before the cracking treatment step, and the above isomerization treatment step was carried out again. More specifically, in Example 1, the isomerization treatment step for 72 days and the cracking treatment step for 24 hours were alternately carried out in a repetitive manner. The catalyst life of the hydroisomerization catalyst in Example 1 was calculated by the following method.

<Evaluation of Hydroisomerization Catalyst Life>

When the reactivity declined as the hydroisomerization catalyst was deactivated, the normal paraffin conversion defined in the above formula (I) drops from 100%. The reaction temperature at the isomerization treatment step was then increased stepwise from Tc (° C.) so that the normal paraffin conversion became 100%, and the operation time required for the reaction temperature to reach 350° C. in the isomerization treatment step was determined. The operation time was evaluated as the catalyst life. The result was as shown in Table 2.

Example 2

The cracking treatment step was carried out once 72 days after the isomerization treatment step was started, and the test was carried out in the same manner as Example 1, except that the cracking treatment step was not carried out thereafter (only the isomerization treatment step was carried out thereafter), thereby calculating the catalyst life of the hydroisomerization catalyst. The result was as shown in Table 2.

Example 3

In the cracking treatment step, the test was carried out in the same manner as Example 1, except that the reaction temperature was selected to give the cracking rate of 15 mass % (353° C.), thereby calculating the catalyst life of the hydroisomerization catalyst. The result was as shown in Table 2.

Example 4

The test was carried out in the same manner as Example 1, except that catalyst E-2 was used in place of catalyst E-1, thereby calculating the life of the hydroisomerization catalyst. The result was as shown in Table 2.

Example 5

The test was carried out in the same manner as Example 1, except that catalyst E-3 was used in place of catalyst E-1, thereby calculating the catalyst life of the hydroisomerization catalyst. The result was as shown in Table 2.

Comparative Example 1

The catalyst life of the hydroisomerization catalyst, when only the isomerization treatment step was carried out without conducting the cracking treatment step at all, was calculated. The result was as shown in Table 2.

Comparative Example 2

In the cracking treatment step, the test was carried out in the same manner as Example 1, except that the reaction temperature was selected to give the cracking rate of 12 mass % (344° C.), thereby calculating the catalyst life of the hydroisomerization catalyst. The result was as shown in Table 2.

TABLE 2

|  | Catalyst | Cracking rate in Second step | Reaction initial temperature Tc (° C.) | Catalyst life (days) |
|---|---|---|---|---|
| Example 1 | E-1 | 30 mass % | 320 | 760 |
| Example 2 | E-1 | 30 mass % | 320 | 643 |
| Example 3 | E-1 | 15 mass % | 320 | 634 |
| Example 4 | E-2 | 30 mass % | 315 | 710 |
| Example 5 | E-3 | 30 mass % | 320 | 690 |
| Comparative Example 1 | E-1 | — | 320 | 620 |
| Comparative Example 2 | E-1 | 12 mass % | 320 | 622 |

As shown in Table 2, in Examples 1 to 5 wherein the first step of isomerization treatment step and the second step of cracking treatment step were carried out, the longer catalyst life performance of the hydrogenation dewaxing catalysts was achieved in comparison with Comparative Example 1 wherein the cracking treatment step was not carried out, thereby enabling to stably obtain a lubricant base oil for a longer period of time. However, Comparative Example 2, in which conditions such that the cracking rate was below 13 mass % in the cracking treatment step was employed, almost failed to obtain the effect for providing the longer catalyst life performance.

The invention claimed is:

1. A method for producing a lubricant base oil, comprising:

a first step of carrying out isomerization dewaxing by contacting, in the presence of hydrogen, a hydrocarbon oil containing normal paraffin having a boiling point of 360° C. or higher, with a hydroisomerization catalyst under conditions such that a cracking rate defined in the following formula (1) is 10 mass % or less; and a second step of carrying out the isomerization dewaxing by temporarily switching the conditions to conditions such that the cracking rate is 13 mass % or more, $$\text{Cracking rate(mass \%)} = [(C_1 - C_2)/C_1] \times 100 \quad (1)$$

wherein $C_1$ represents a mass ratio of a fraction having a boiling point of 360° C. or higher in the hydrocarbon oil, and $C_2$ represents the mass ratio of the fraction having a boiling point of 360° C. or higher in the hydrocarbon oil after the isomerization dewaxing.

2. The method for producing a lubricant base oil according to claim 1, wherein the hydroisomerization catalyst is a catalyst containing a zeolite having a one-dimensional porous structure including a 10-membered ring, a support containing a binder, and platinum and/or palladium supported on the support;

a carbon content of the catalyst is 0.4 to 3.5% by mass;

the zeolite is derived from an ion-exchanged zeolite obtained by ion-exchanging an organic template-containing zeolite containing an organic template and having a one-dimensional porous structure including a 10-membered ring in a solution containing ammonium ions and/or protons.

3. The method for producing a lubricant base oil according to claim 1, wherein the hydroisomerization catalyst is a catalyst containing a zeolite having a one-dimensional porous structure including a 10-membered ring, a support containing a binder, and platinum and/or palladium supported on the support;

a micropore volume per unit mass of the catalyst is 0.02 to 0.12 cc/g;

the zeolite is derived from an ion-exchanged zeolite obtained by ion-exchanging an organic template-containing zeolite containing an organic template and having a one-dimensional porous structure including a 10-membered ring in a solution containing ammonium ions and/or protons; and a micropore volume per unit mass of the zeolite contained in the catalyst is 0.01 to 0.12 cc/g.

4. The method for producing a lubricant base oil according to claim 1, wherein while performing the first step continuously, the second step is temporarily carried out at predetermined intervals.

* * * * *